US 6,613,096 B1

(12) United States Patent
Shirvis

(10) Patent No.: US 6,613,096 B1
(45) Date of Patent: Sep. 2, 2003

(54) PROSTHETIC PRESSURE RELIEF VALVE SYSTEM

(76) Inventor: Raymond A. Shirvis, 12551 Vonn Rd., Largo, FL (US) 33774

(*) Notice: Subject to any disclaimer, the term of this patent is extended or adjusted under 35 U.S.C. 154(b) by 0 days.

(21) Appl. No.: 10/117,642

(22) Filed: Apr. 5, 2002

(51) Int. Cl.[7] .................................................. A61F 2/80
(52) U.S. Cl. ..................... 623/34; 251/174; 251/185; 251/227; 137/542
(58) Field of Search ...................... 623/32–37; 251/174, 251/176, 185, 227; 137/542

(56) References Cited

U.S. PATENT DOCUMENTS

| | | | | | |
|---|---|---|---|---|---|
| 2,530,285 | A | * | 11/1950 | Catranis | 3/3 |
| 2,533,404 | A | * | 12/1950 | Sharp et al. | 3/9 |
| 2,790,180 | A | * | 4/1957 | Hauser | 3/1 |
| 4,168,723 | A | * | 9/1979 | Schneider | 137/542 |
| 4,294,409 | A | * | 10/1981 | Larsen | 239/577 |
| 6,287,345 | B1 | * | 9/2001 | Slemker et al. | 623/34 |

\* cited by examiner

*Primary Examiner*—Bruce Snow
(74) *Attorney, Agent, or Firm*—Edward P. Dutkiewicz

(57) ABSTRACT

A cylindrical housing has a flange at an exterior end, male threads in an external surface remote from the flange, and a small axial hole, and female threads in an internal surface remote from the flange. A disk shaped fastener has internal threads rotatably supported upon the male threads of the housing. The fastener rotates to secure a prosthetic limb adjacent to the flange for operation and use and to allow separation of the limb from the housing. A cup-shaped end plug has a side wall with male threads receivable in the female threads of the housing and an end face with an axial opening. A plug with a pull string is positionable within a partly spherical surface adjacent to the interior end of the housing. A coil spring is positioned between the end plug and the spherical plug.

4 Claims, 3 Drawing Sheets

PROSTHETIC PRESSURE RELIEF VALVE SYSTEM

BACKGROUND OF THE INVENTION

1. Field of the Invention

The present invention relates to a prosthetic pressure relief valve system and more particularly pertains to allowing a user to attach and remove a prosthetic limb safely and conveniently.

2. Description of the Prior Art

The use of prosthetic pressure relief valve systems of known designs and configurations is known in the prior art. More specifically, prosthetic pressure relief valve systems of known designs and configurations previously devised and utilized for the purpose of attaching and removing prosthetic limbs are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,490,537 to Hill discloses a prosthesis air valve assembly and tool therefor. U.S. Pat. No. 5,658,353 to Layton discloses a method for donning or doffing an artificial limb. U.S. Pat. No. 2,533,404 to Sharp et al discloses an artificial limb and valve therefor. U.S. Pat. No. 2,790,180 to Hauser discloses an artificial limb and valve therefor. Finally, U.S. Pat. No. 6,287,345 to Slemker et al discloses a valve assembly for a prosthetic limb.

While these devices fulfill their respective, particular objectives and requirements, the aforementioned patents do not describe a prosthetic pressure relief valve system that allows a user to attach and remove a prosthetic limb safely and conveniently.

In this respect, the prosthetic pressure relief valve system according to the present invention substantially departs from the conventional concepts and designs of the prior art, and in doing so provides an apparatus primarily developed for the purpose of allowing a user to attach and remove a prosthetic limb safely and conveniently.

Therefore, it can be appreciated that there exists a continuing need for a new and improved prosthetic pressure relief valve system which can be used for attaching and removing a prosthetic limb safely and conveniently. In this regard, the present invention substantially fulfills this need.

SUMMARY OF THE INVENTION

In view of the foregoing disadvantages inherent in the known types of prosthetic pressure relief valve systems of known designs and configurations now present in the prior art, the present invention provides an improved prosthetic pressure relief valve system. As such, the general purpose of the present invention, which will be described subsequently in greater detail, is to provide a new and improved prosthetic pressure relief valve system and method which has all the advantages of the prior art and none of the disadvantages.

To attain this, the present invention essentially comprises a prosthetic limb. The prosthetic limb has an exposed outer surface and an interior surface adapted to removably receive an end of a user's limb. An aperture is provided through the prosthetic limb. A cylindrical housing has an internal surface and an external surface. The housing also has an interior end. An exterior end of the housing is formed with a flange. Male threads are formed in the external surface remote from the flange. A small axial hole is formed in the housing. Female threads are formed in the internal surface remote from the flange. Next provided is a disk shaped fastener with internal threads rotatably supported upon the male threads of the housing. The fastener is rotatable in a first direction to secure the prosthetic limb adjacent to the flange for operation and use. The fastener is rotatable in a second direction to allow separation of the prosthetic limb from the housing. An end plug in a cup shaped configuration is next provided. The end plug has a side wall formed with male threads receivable in the female threads of the housing. The end plug also has an end face formed with an axial opening. Next provided is a partly spherical surface adjacent to the interior end of the housing. A spherical plug is positionable within the spherical surface. A coil spring is positioned between the end plug and the spherical plug. A pull string is provided. An end of the pull string is attached to the spherical plug. A center section of the string is positioned within the coil spring and is knotted. The knot functions to limit a user from applying too much tension and pulling the string out of the spherical plug. An exterior section of the string extends through the axial opening in the end plug. In this manner donning the prosthetic limb will remove air and cause a suction between the valve system and the prosthetic limb. Pulling the string will separate the plug from the spherical surface to allow removing the prosthetic limb.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved prosthetic pressure relief valve system which has all of the advantages of the prior art prosthetic pressure relief valve systems of known designs and configurations and none of the disadvantages.

It is another object of the present invention to provide a new and improved prosthetic pressure relief valve system which may be easily and efficiently manufactured and marketed.

It is further an object of the present invention to provide a new and improved prosthetic pressure relief valve system which is of durable and reliable constructions.

An even further object of the present invention is to provide a new and improved prosthetic pressure relief valve system which is susceptible of a low cost of manufacture with regard to both materials and labor, and which accordingly is then susceptible of low prices of sale to the consuming public, thereby making such prosthetic pressure relief valve system economically available to the buying public.

Even still another object of the present invention is to provide a prosthetic pressure relief valve system for allowing a user to attach and remove a prosthetic limb safely and conveniently.

Lastly, it is an object of the present invention to provide a new and improved cylindrical housing with a flange at an exterior end, male threads in an external surface remote from the flange, and a small axial hole, female threads in an internal surface remote from the flange. A disk shaped fastener has internal threads rotatably supported upon the male threads of the housing. The fastener rotates to secure a prosthetic limb adjacent to the flange for operation and use and to allow separation of the limb from the housing. A cup-shaped end plug has a side wall with male threads receivable in the female threads of the housing and an end face with an axial opening. A plug with a pull string is positionable within a partly spherical surface adjacent to the interior end of the housing. A coil spring is positioned between the end plug and the spherical plug.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
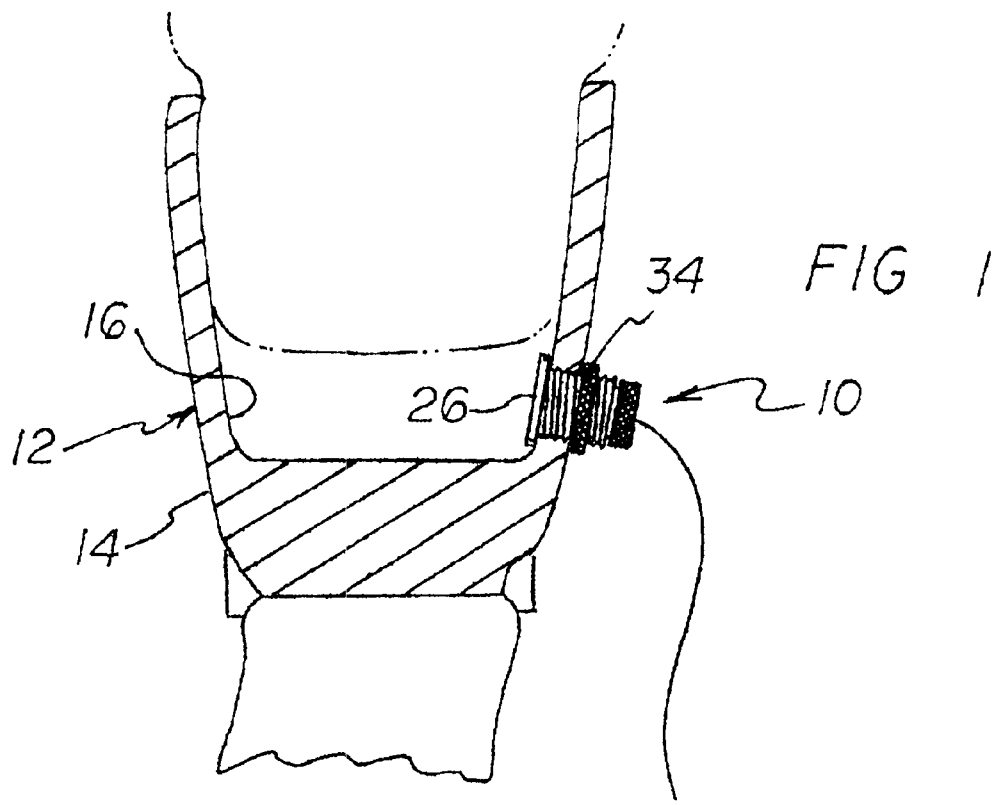
FIG. 1 is a cross-sectional view of the prosthetic pressure relief valve system constructed in accordance with the principles of the present invention showing the system in operation and use.
Figure 2:
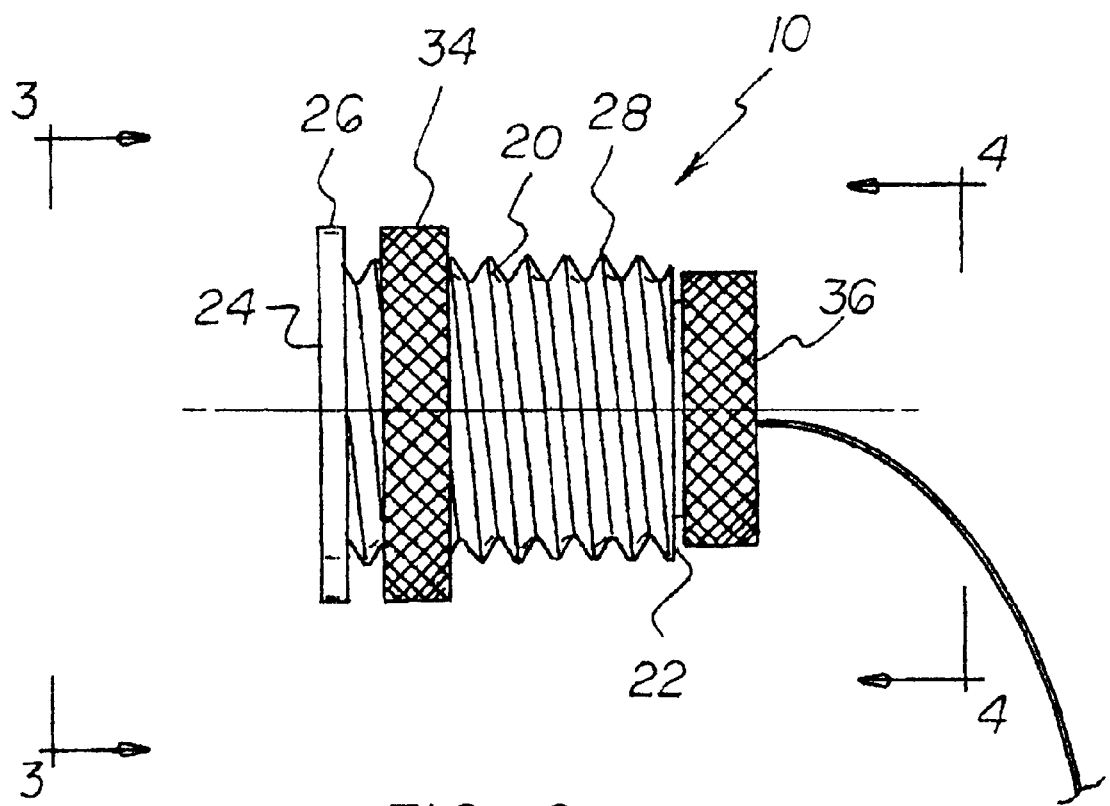
FIG. 2 is a side elevational view of the housing of the system of FIG. 1.
Figure 3:
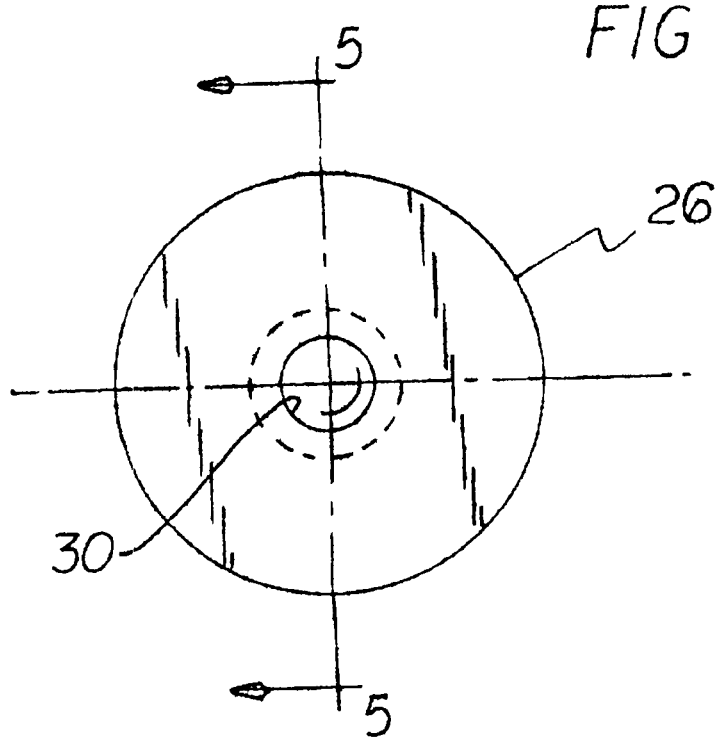
FIG. 3 is a left end view taken along line 3—3 of FIG. 2.
Figure 4:
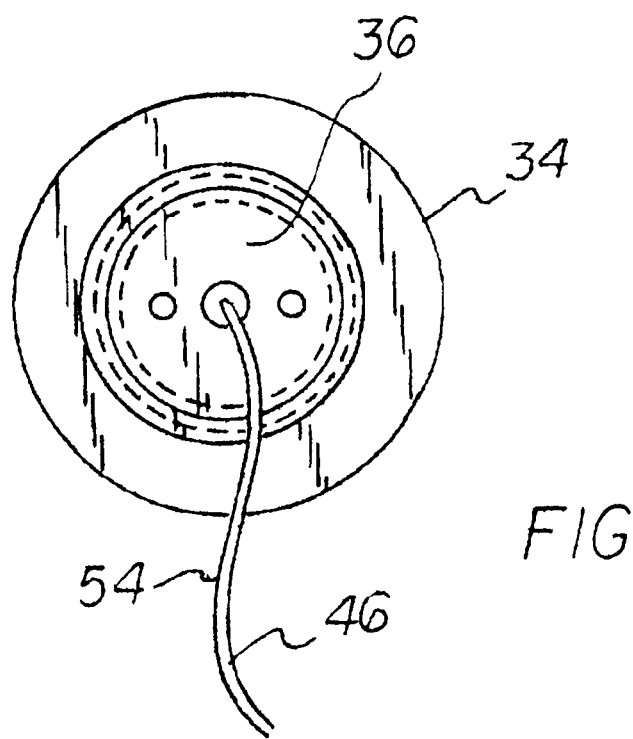
FIG. 4 is a right end view taken along line 4—4 of FIG. 2.
Figure 5:
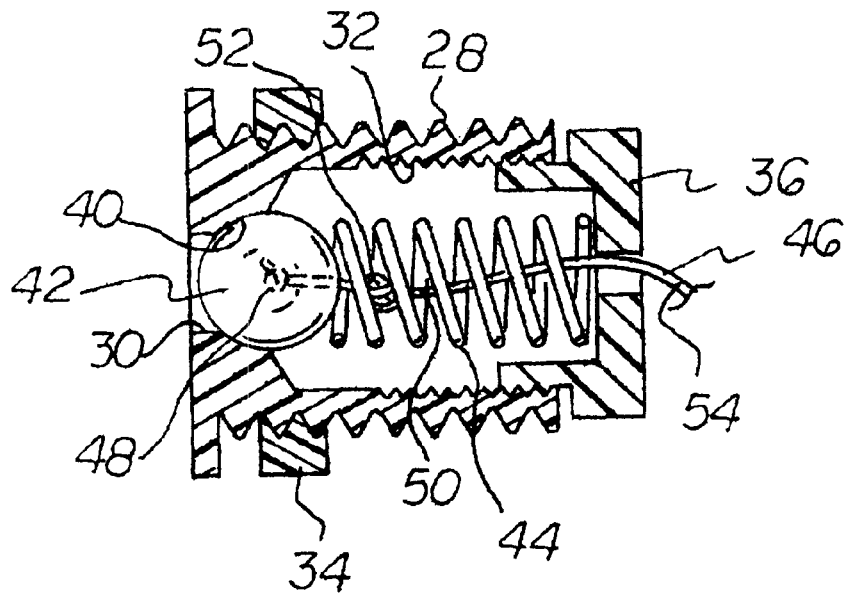
FIG. 5 is a cross-sectional view of the prosthetic relief valve system of the present invention.

With reference now to the drawings, and in particular to FIG. 1 thereof, the preferred embodiment of the new and improved prosthetic pressure relief valve system embodying the principles and concepts of the present invention and generally designated by the reference numeral 10 will be described.

The present invention, the prosthetic pressure relief valve system 10 is comprised of a plurality of components. Such components in their broadest context include a cylindrical housing, a disk shaped fastener, an end plug, a partly spherical surface and a pull string. Such components are individually configured and correlated with respect to each other so as to attain the desired objective.

First provided is a prosthetic limb 12. The limb has an exposed outer surface 14 and an interior surface 16 adapted to removably receive an end of a user's limb. An aperture is provided through the prosthetic limb.

A cylindrical housing 20 has an internal surface and an external surface. The housing also has an interior end 24. An exterior end 22 of the housing is formed with a flange 26. Male threads 28 are formed in the external surface remote from the flange. A small axial hole 30 is formed in the housing. Female threads 32 are formed in the internal surface remote from the flange.

Next provided is a disk shaped fastener 34 with internal threads rotatably supported upon the male threads of the housing. The fastener is rotatable in a first direction to secure the prosthetic limb adjacent to the flange for operation and use. The fastener is rotatable in a second direction to allow separation of the prosthetic limb from the housing.

An end plug 36 in a cup shaped configuration is next provided. The end plug has a side wall formed with male threads receivable in the female threads of the housing. The end plug also has an end face formed with an axial opening.

Next provided is a partly spherical surface 40 adjacent to the interior end of the housing. A spherical plug 42 is positionable within the spherical surface. A coil spring 44 is positioned between the end plug and the spherical plug. A pull string 46 is provided. The pull string is positioned within the coil spring. An end 48 of the pull string is attached to the spherical plug. A center section 50 of the string is positioned within the coil spring and is knotted. The knot 52 functions to limit a user from applying too much tension and pulling the string out of the spherical plug. An exterior section 54 of the string extends through the axial opening in the end plug. In this manner donning the prosthetic limb will remove air and cause a suction between the valve system and the prosthetic limb and pulling the string will separate the plug from the spherical surface to allow removing the prosthetic limb.

Figure 6:
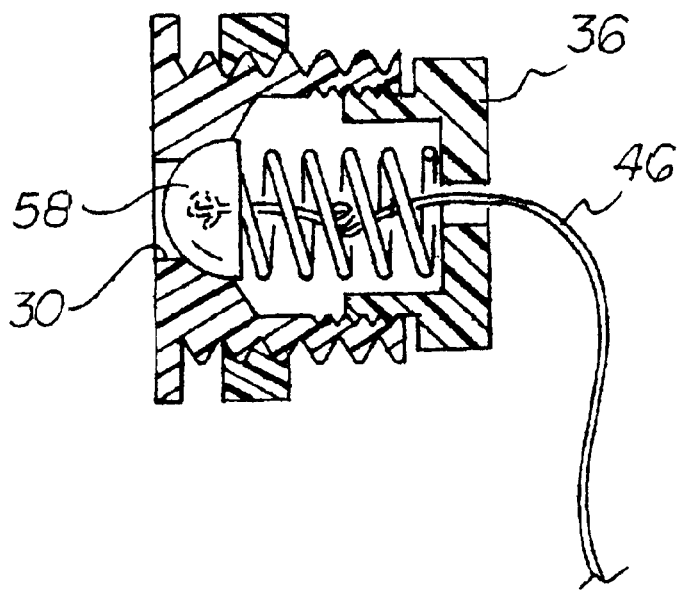
FIG. 6 is a cross-sectional view of a less obtrusive alternate embodiment of the invention in which the plug is in the shape of a cabochon and the length of the housing is reduced.

An alternate embodiment of the system is shown in FIG. 6. In this embodiment, the plug 58 is in the shape of a cabochon, or half stone. The housing of this embodiment is reduced in length. This lower profile allows the system to be less obtrusive.

In an additional alternate embodiment of the system the valve is a one-way valve. In this embodiment, the pull string is eliminated.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A prosthetic pressure relief valve system comprising:
   a cylindrical housing having an internal surface and an external surface and an interior end and an exterior end, formed with a flange with male threads formed in the external surface remote from the flange, a small axial hole formed in the housing with female threads formed in the internal surface remote from the flange;
   a disk shaped fastener with internal threads rotatably supported upon the male threads of the housing, the fastener being rotatable in a first direction to secure a prosthetic limb adjacent to the flange for operation and use, the fastener being rotatable in a second direction to allow separation of the prosthetic limb from the housing;
   an end plug in a cup shaped configuration with a side wall formed with male threads receivable in the female threads of the housing and also formed with an end face formed with an axial opening; and
   a partly spherical surface adjacent to the interior end of the housing with a plug positionable within the spherical surface and a coil spring positioned between the end plug and the spherical plug with a pull string.

2. The system as set forth in claim 1 wherein the plug is spherical in shape.

3. The system as set forth in claim 1 wherein the plug is less than hemispherical in shape.

4. A prosthetic pressure relief valve system 10 for safely and conveniently allowing a user to attach or remove a prosthetic limb comprising, in combination:
   a prosthetic limb having an exposed outer surface and an interior surface adapted to removably receive an end of a user's limb, the prosthetic limb having an aperture there through;
   a cylindrical housing having an internal surface and an external surface and an interior end and an exterior end, formed with a flange with male threads formed in the external surface remote from the flange, a small axial hole formed in the housing with female threads formed in the internal surface remote from the flange;
   a disk shaped fastener with internal threads rotatably supported upon the male threads of the housing, the fastener being rotatable in a first direction to secure the prosthetic limb adjacent to the flange for operation and use, the fastener being rotatable in a second direction to allow separation of the prosthetic limb from the housing;
   an end plug in a cup shaped configuration with a side wall formed with male threads receivable in the female threads of the housing and also formed with an end face formed with an axial opening; and
   a partly spherical surface adjacent to the interior end of the housing with a spherical plug positionable within the spherical surface and a coil spring positioned between the end plug and the spherical plug;
   a pull string positioned within the coil spring having an end attached to the spherical plug, a knotted center section, and an exterior section extending through the axial opening in the end plug, whereby donning the prosthetic limb will remove air and cause a suction between the valve system and the prosthetic limb while pulling the string will separate the plug from the spherical surface to allow removing the prosthetic limb.

\* \* \* \* \*